United States Patent [19]
Sutton

[11] Patent Number: 5,472,435
[45] Date of Patent: Dec. 5, 1995

[54] DRAINAGE CATHETER

[75] Inventor: Gregg S. Sutton, Maple Grove, Minn.

[73] Assignee: Navarre Biomedical, Ltd., Plymouth, Minn.

[21] Appl. No.: 65,806

[22] Filed: May 21, 1993

[51] Int. Cl.$^6$ ................................................ A61M 25/00
[52] U.S. Cl. ............................................. 604/282; 604/280
[58] Field of Search ................................... 604/282, 280, 604/264, 281, 283

[56] References Cited

U.S. PATENT DOCUMENTS

| | | | |
|---|---|---|---|
| 3,416,531 | 12/1968 | Edwards | 128/348 |
| 3,426,744 | 2/1969 | Ball | 128/1 |
| 3,477,474 | 11/1969 | Mesler | 138/133 |
| 3,485,234 | 12/1969 | Stevens | 128/2 |
| 3,618,613 | 11/1971 | Schulte . | |
| 3,840,384 | 10/1974 | Reade et al. | 117/8 |
| 3,861,396 | 1/1975 | Vaillancourt et al. | 128/350 |
| 3,865,776 | 2/1975 | Gergen | 260/33.6 |
| 4,140,154 | 2/1979 | Kanao | 138/132 |
| 4,167,953 | 9/1979 | Carlstrom | 138/133 |
| 4,172,473 | 10/1979 | Lefere et al. | 138/120 |
| 4,368,730 | 1/1983 | Sharrock . | |
| 4,405,314 | 9/1983 | Cope . | |
| 4,623,329 | 11/1986 | Drobish et al. . | |
| 4,634,432 | 1/1987 | Kocak | 604/167 |
| 4,639,252 | 1/1987 | Kelly et al. | 604/282 |
| 4,817,613 | 4/1989 | Jaraczewski et al. | 128/658 |
| 4,863,441 | 9/1989 | Lindsay et al. . | |
| 4,898,591 | 2/1990 | Jang et al. | 604/282 |
| 4,990,143 | 2/1991 | Sheridan . | |
| 5,002,528 | 3/1991 | Palestrant . | |
| 5,015,238 | 5/1991 | Solomon et al. . | |
| 5,019,057 | 5/1991 | Truckai | 604/282 |
| 5,041,085 | 8/1991 | Osborne et al. . | |
| 5,059,375 | 10/1991 | Lindsay | 264/167 |
| 5,061,257 | 10/1991 | Martinez et al. | 604/282 |
| 5,064,417 | 11/1991 | Andreussi . | |
| 5,125,895 | 6/1992 | Buchbinder et al. . | |
| 5,163,431 | 11/1992 | Griep | 604/282 |
| 5,180,376 | 1/1993 | Fischell . | |
| 5,201,723 | 4/1993 | Quinn | 604/282 |
| 5,209,742 | 5/1993 | Venema et al. | 604/281 |
| 5,221,255 | 6/1993 | Mahurkar et al. | 604/282 |

FOREIGN PATENT DOCUMENTS

| | | | |
|---|---|---|---|
| 278937 | 8/1988 | European Pat. Off. | 604/281 |
| 9011793 | 10/1990 | WIPO | 604/282 |

*Primary Examiner*—John G. Weiss
*Attorney, Agent, or Firm*—Gregory P. Kaihoi

[57] ABSTRACT

A kink resistant multi-purpose drainage catheter. A drainage catheter is constructed using kink resistant tubing. One end of the kink resistant tube forms a drain for bodily fluids. The opposite end of the kink resistant tube has a molded LUER connector. The drain has numerous holes along its length to allow drainage. The substrate of the kink resistant tube is constructed from an extrusion. The extrusion is then covered with a coil along the body of the catheter. The entire length of the drainage catheter is coated with a final layer of polyurethane. The drain may be formed in a number of desired shapes along with the position of drainage holes.

11 Claims, 9 Drawing Sheets

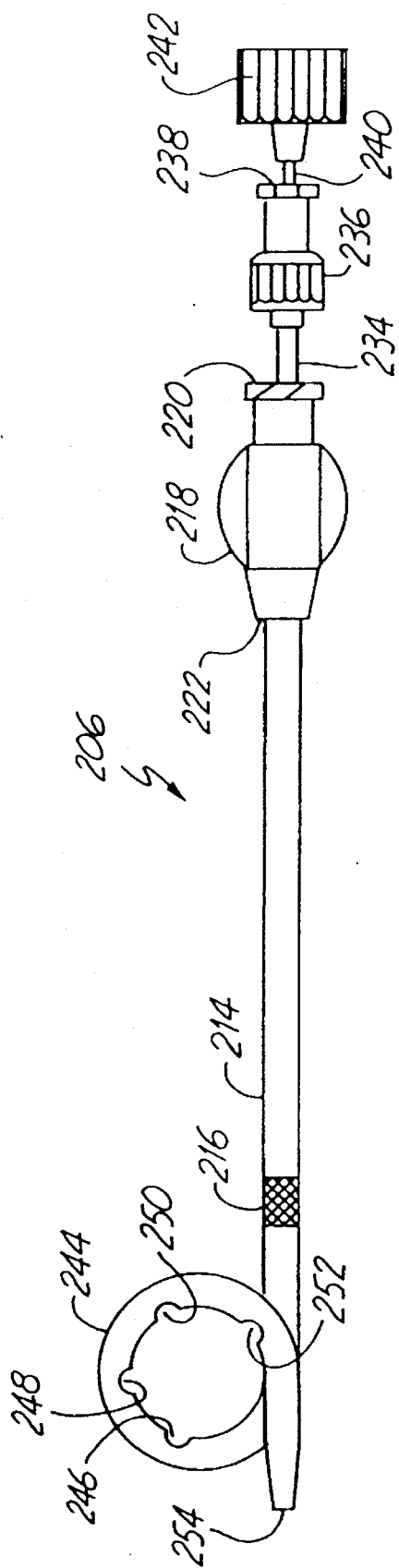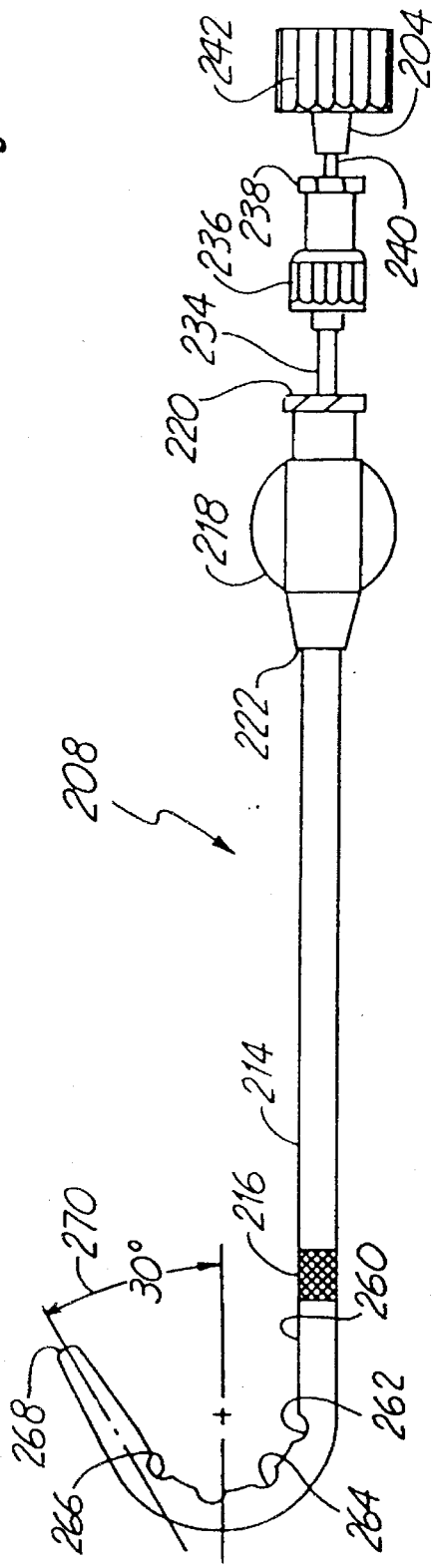

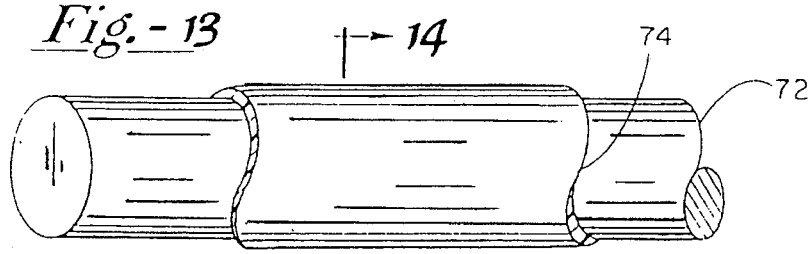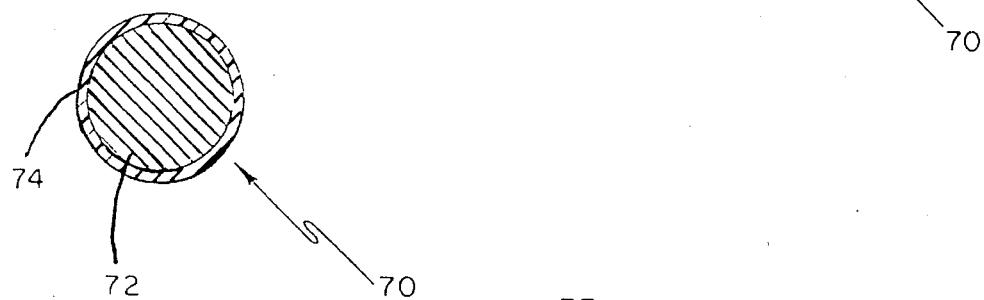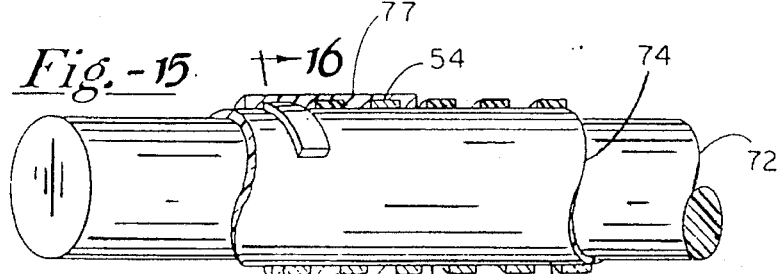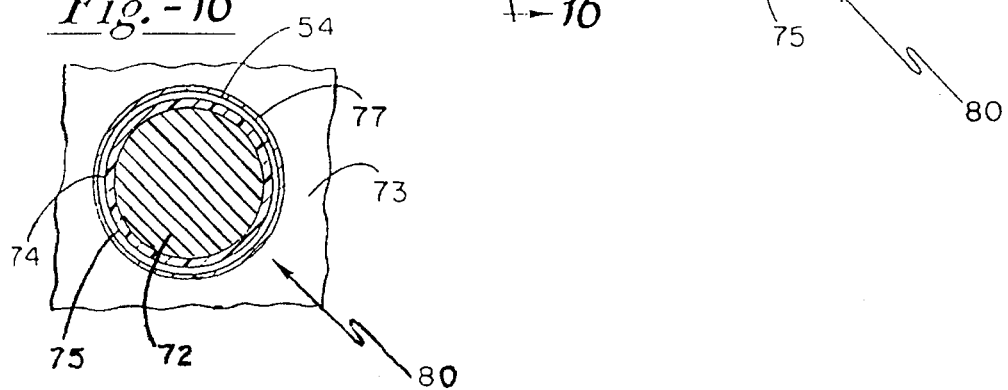

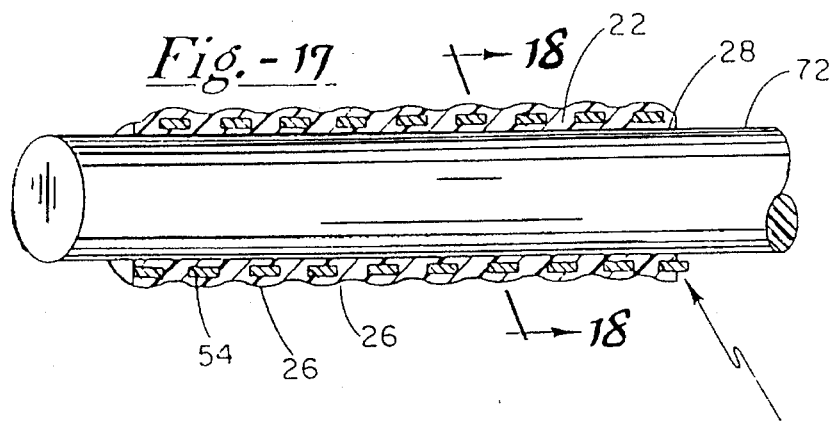
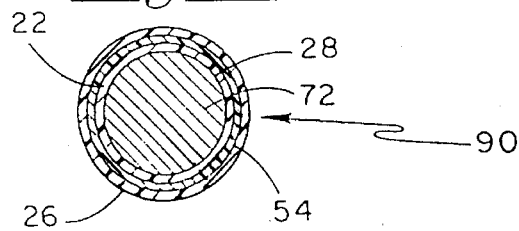
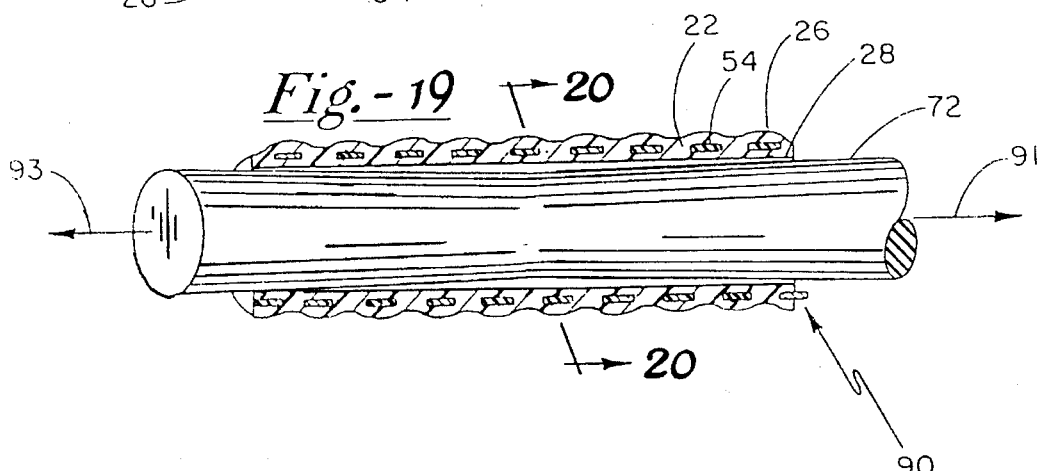
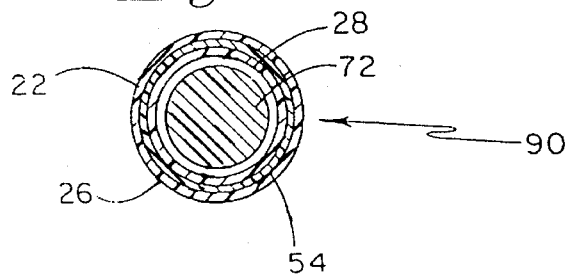

DRAINAGE CATHETER

This invention relates to a multi-purpose drainage catheter and, more particularly, to a kink resistant multipurpose drainage catheter useful for percutaneous drainage of abdominal abscesses, cysts, and other fluid collections including nephrostomes.

BACKGROUND OF THE INVENTION

The prior art shows numerous drainage catheters and a non-buckling thin-walled sheath. The prior art does not show a kink resistant multi-purpose drainage catheter.

Drainage catheters may be employed in order to percutaneously drain fluid from cavities of the body. For example they may be used to drain abdominal fluid collections from the peritoneal cavity and pleural cavity. These fluids may include ascites fluid that builds up as a result of cirrhosis or malignancies such as ovarian cancer. Drainage catheters can also be used for post surgical drainage of fluid after laparotomy or cholecystectomy. In the pleural cavity, drainage catheters can also be used to drain effusions. Effusions can result from malignancy, lymphangiectasis, catogenic or congenital chylothorax, as well as other types of well-known conditions.

U.S. Pat. No. 5,180,376 to Fischell, entitled "Non-Buckling Thin-Walled Sheath For the Percutaneous Insertion of Intraluminal Catheters," describes a non-buckling thin-walled sheath for the percutaneous insertion of intraluminal catheters. The patent describes an introducer sheath having an extremely thin, flat wire metal coil that is surrounded only on its exterior surface with a plastic tube or coating. The flat wire coil optimizes the resistance of the sheath to buckling while minimizing the wall thickness of the sheath. The plastic covering being limited to the outside of the metal coil optimizes the thinness of the introducer sheath. The device is an introducer with an alternative embodiment consisting of two flat wire metal coils, one wound over the other.

U.S. Pat. No. 5,125,895 to Buchbinder, et al., entitled "Steerable Catheter," describes a flexible catheter having a spring coil body defining a lumen, the spring coil body having a flexible covering and a deflection wire. The distal end of the deflection wire is attached to the distal end of the spring coil body and to the proximal end of the catheter. The proximal end of the deflection wire extends through the control means and the control means has a port means which engages the deflection wire.

U.S. Pat. No. 5,064,417 to Andreussi, entitled "Device for Fastening a Catheter to a Cranial Theca for Performing Cerebro Spinal Fluid Drainage to the Outside Operations" describes a device for fastening a catheter to a cranial theca for performing cerebro spinal fluid drainage to the outside operations. The device is a mechanism for fastening a catheter to an osteofibrous wall for draining cerebro spinal fluid.

U.S. Pat. No. 5,015,238 to Solomon, et al., entitled "Expandable Obturator and Catheter Assembly Including Same," describes an expandable obturator and catheter assembly. The obturator has a stiff rod of non-hydrophilic polyurethane, coated with a layer of hydrophilic polyurethane. The hydrophilic polyurethane may have an antithrombogenic agent. When the obturator is in place and the catheter is brought into contact with the liquid, it expands, releasing the antithrombogenic agent and contacting the lumen wall of the catheter, thereby forming a seal which prevents backflow of a body fluid.

U.S. Pat. No. 5,002,528 to Palestrant, entitled "Percutaneous Irrigation and Drainage System," describes a percutaneous irrigation and drainage system. The system is a closed system for percutaneous irrigation and drainage of cavities containing abscesses, sterile fluid collections or hematomas including an irrigant reservoir. An irrigation tube connects the reservoir to a port and multi-port member adapted to fluidically connect two of the three ports at a time. The distal end of the drainage catheter is adapted to be placed in the cavity. The proximal end of the catheter is connected to the second port of the second connector. A drainage tube is connected to the third port of the second connector, which is in turn connected to a means for collecting fluids draining from the cavity.

U.S. Pat. No. 4,623,329 to Drobish, et al., entitled "Drainage and Infusion Catheters Having a Capillary Sleeve Forming a Reservoir For a Fluid Antimicrobial Agent," describes a drainage and infusion catheter having a capillary sleeve forming a reservoir. The catheter has an elongated tubular shaft, the distal end of which is provided with at least one port. A sleeve is mounted about the shaft, extending along a portion of the internal body surface. The inner surface of the sleeve is provided with a plurality of longitudinally extending capillary channels or grooves, providing uniform distribution of the fluid antimicrobial agent within the reservoir and throughout the length of the reservoir.

U.S. Pat. No. 4,405,314, to Cope, entitled "Apparatus and Method For Catheterization Permitting Use of A Smaller Gage Needle," describes an apparatus and method for catheterization permitting use of a smaller gage needle. An introducing catheter for use with a pair of different diameter wire guides is described. The larger of the wire guides is a J-type wire guide. The J-type guide is provided to enlarge a tract in order to facilitate the passage of drainage catheters through the tract. The introducing catheter includes an inwardly curved portion which lies between the distal and proximal ends of the catheter, with the curved portion being located nearer to the distal end. The catheter has a side port which is distally positioned from the curved portion, and on the inward side of the curved portion, so that a J-type wire guide is advanced within the catheter from the proximal end. The wire guide can automatically emerge from the side port. The side port has an oval or elliptical shape with the major axis along the length of the tube.

Therefore, it is the motivation of the invention to provide a kink resistant multi-purpose drainage catheter that has superior drainage in vivo ability to drain fluids from the body.

SUMMARY OF THE INVENTION

The invention provides a kink resistant multi-purpose drainage catheter. The body of the kink resistant drainage catheter comprises a kink resistant tube made from an extruded substrate with a reinforcing coil wound around part of the extruded substrate. The nonreinforced and reinforced extruded substrate is then covered with a plastic tube or coating. A LUER connector is attached to the proximal end of the kink resistant tube by adhesives or by mold injection. A curve of a predetermined radius and angle is formed by a heating process at the distal end of the kink resistant tube. Three to six drainage holes are formed along the curve and a tappered end, with a central drain hole, is thermally formed at the extreme distal end of the covered extruded substrate.

The kink resistant multi-purpose drainage catheter provides a single lumen passageway for the percutaneous drainage of fluids. The distal end is designed in alternate embodiments to effect drainage and improve retention in more than one manner. In one alternate embodiment, the distal end is straight, in another, the distal end makes a loop forming a pigtail. In yet another alternate embodiment, the distal end forms a "J".

For insertion into the body, a cannula is inserted within the drainage catheter and a needle stylet is inserted within the cannula. The needle stylet makes the initial puncture while the cannula stiffens and protects the drainage catheter during insertion in the body.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIG. 2 shows a schematic side view of an alternate embodiment of the invention with a pig-tail drainage end.

FIG. 3 shows a schematic side view of another alternate embodiment of the invention with a "J" drainage end.

FIG. 13 shows the first step of manufacturing the kink resistant tubing used in the drainage catheter apparatus of the invention, showing a mandrel both coated with a thin layer of encapsulating material and also with the encapsulating material cut away.

FIG. 14 shows a cross-section of a mandrel with a thin layer of encapsulating material.

FIG. 15 shows a mandrel and a thin layer of encapsulating material with a cut away of the coil wound around the thin layer of encapsulating material.

FIG. 16 shows a kink resistant tubing cross-sectional diagram with a reinforcing coil wrapped around the thin encapsulating layer.

FIG. 17 shows the kink resistant tube in its final constructed state on the mandrel.

FIG. 18 shows a cross-section of the mandrel with the kink resistant tube in its final constructed state.

FIG. 19 shows the method of removing the kink resistant tubing from the mandrel.

FIG. 20 shows the kink resistant tubing being removed from the mandrel in a cross sectional view.

DETAILED DESCRIPTION OF THE PREFERRED EMBODIMENT

Figure 1A:
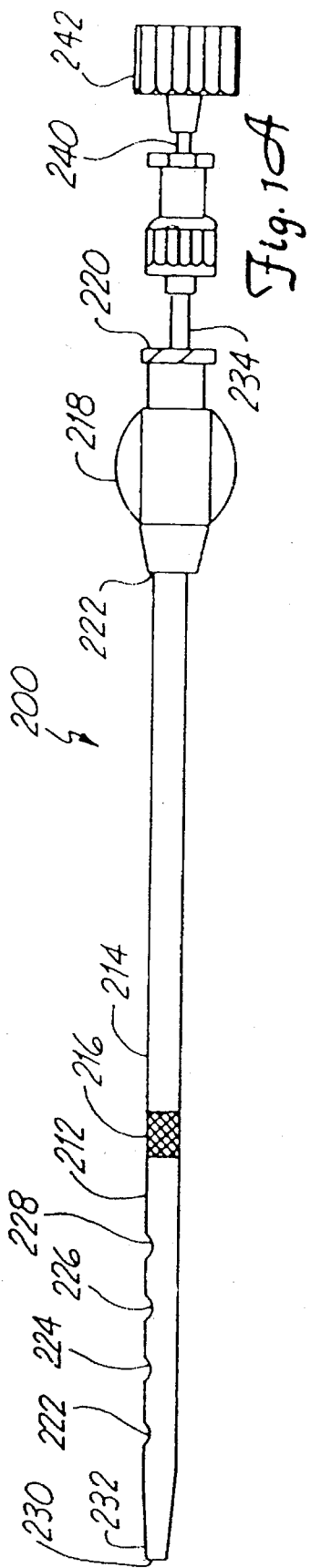
FIGS. 1A, 1B and 1C show a schematic side view of the drainage catheter apparatus of the invention with a cannula and a stylet.

Referring now to FIG. 1A, FIG. 1A shows a schematic side view of the drainage catheter of the invention. The drainage catheter 200 is comprised of, a kink resistant tube with an integral drainage end and a LUER connector. The drainage end 212 is formed from one end of a covered or coated substrate. The substrate could be constructed by extrusion or by the coating of a mandrel. The drainage end 212 has a number of holes 222, 224, 226 and 228. The holes provide drainage areas to allow fluids to drain into the lumen of the drainage catheter 200. The drainage end 232 has an orifice 230 which provides additional drainage for the drainage catheter 200. The drainage catheter 200 may be manipulated during connection to other drainage devices by a LUER connector 218 which may be of any various geometries as commonly known to those skilled in the art. The LUER connector 218 may be adhesively attached or thermally bonded to kink resistant tube 222 to provide a strong and durable connection. The LUER connector 218 has threads 220 which provides for the secure connection of a cannula 202. The cannula 202 is further described in FIG. 1B. The cannula 202 accepts a styler 204 which is used to insert the drainage catheter in the body.

The drainage end 212 of drainage catheter 200 is provided as straight. Alternate embodiments of the drainage end are provided to allow for improved drainage and for retention.

Figure 1B:
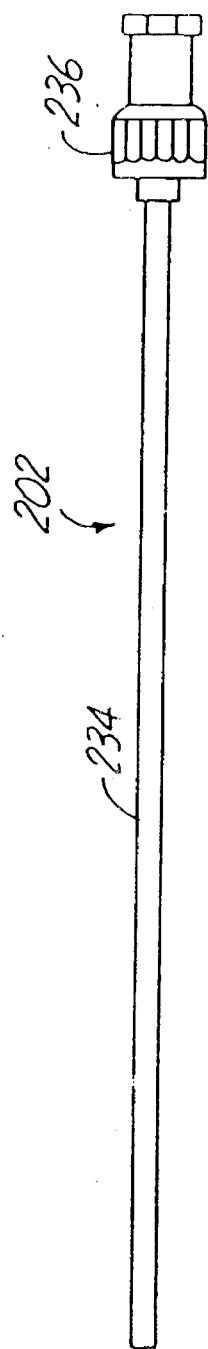

Now referring to FIG. 1B, FIG. 1B shows a cannula used to stiffen the kink resistant multi-purpose drainage catheter of the invention. The cannula is comprised of a stiff tubular material 234 which has a stylet accepting LUER connecting adapter 236. The LUER connecting adapter 236 provides for secure connection of a stylet.

Figure 1C:
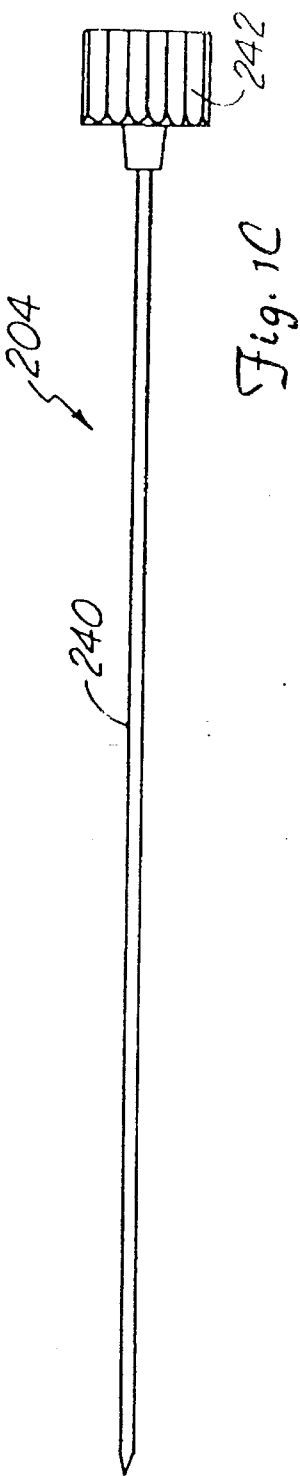

Now referring to FIG. 1C, FIG. 1C shows a stylet 204 used to insert the kink resistant drainage catheter in the body. The stylet 204 is comprised of a pencil point stylus with a manipulable LUER connector 242. The LUER connector 242 may be secured to the stylet LUER connecting adapter 236 of the cannula.

Now that the structure of the drainage catheter of the invention has been disclosed, the function of each element will be described with reference to FIGS. 1A, 1B and 1C. Prior to insertion of the drainage catheter into the body, the cannula 202 is inserted in the drainage catheter 200 and the stylet 204 is inserted in the cannula 202. The point of the stylet 204 protrudes past the drainage end 212 of the drainage catheter. The cannula 202 stiffens the drainage catheter 200 during insertion into the body. The protrusion of the stylet past the drainage end 212 of the drainage catheter provides for relatively easy insertion of the drainage catheter into the body. Once inserted, the cannula and stylet are removed from the drainage catheter and the catheter is free to begin drainage. The kink resistant tube 214 used in the drainage catheter 200 provides a highly reliable means of continuous drainage of fluid from the body. The other drainage tubes of the prior art have problems with kinking and buckling as described above.

Referring now to FIG. 2, FIG. 2 shows an alternate embodiment of the kink resistant drainage catheter of the invention. FIG. 2 shows a pigtail drainage end 244 having holes 246, 248, 250 and 252 placed radially around the pigtail on the inside circumference. The drainage end 244 has a lumen 254 which provides for additional drainage. The pigtail design helps prevent catheter migration by making it harder to pull the catheter out, thereby contributing to the maintenance of a more reliable drainage opening within the body.

The drainage catheter of FIG. 2 is inserted in the same manner as the drainage catheter of FIG. 1A. The stylet 204 is inserted within the LUER connecting adapter 236 of cannula 202 which is then inserted in the drainage catheter 206. The cannula stiffens the kink resistant tube 214 which is flexible. The cannula also straightens out and stiffens the pigtail drainage end 244 during insertion. The pigtail forms when the cannula 202 and LUER connecting adapter 236 is removed.

Now referring to FIG. 3, FIG. 3 shows yet another alternate embodiment of the drainage catheter of the invention. FIG. 3 shows a "J" drainage end 260 which has holes 262, 264 and 266. The drainage end 260 has a lumen 268. The "J" drainage end is formed at a predetermined angle with respect to the kink resistant tube axis angle 270. The "J" drainage end provides improved retention of the catheter in the body.

The drainage catheter of FIG. 3 is constructed similarly to the drainage catheters of FIGS. 1A and 2. Styler 204 is inserted in stiffening cannula 202, and the stiffening cannula 202 is inserted within kink resistant drainage catheter 208. The stiffening cannula 202 straightens out the "J" drainage end 260 during insertion. When the cannula 202 is removed from the kink resistant drainage catheter 208, the "J" tube springs back and provides for effective drainage.

Figure 4:
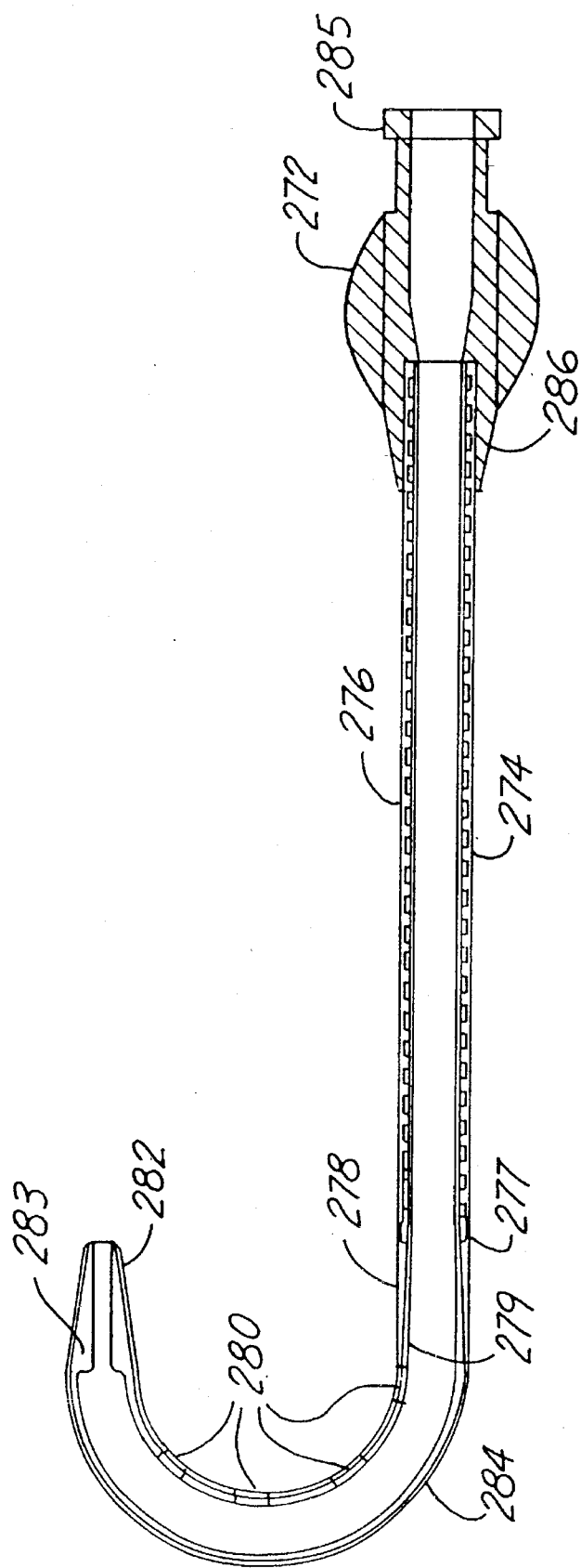
FIG. 4 shows a cross section of yet another alternative embodiment of the multi-purpose kink resistant multi-purpose drainage catheter of the invention.

Now referring to FIG. 4, FIG. 4 shows a cross section of yet another alternative embodiment of the multi-purpose kink resistant drainage catheter of the invention. FIG. 4 shows a kink resistant tube 274 comprised of a plurality of layers and a reinforcement coil 276. The reinforcement coil 276 is terminated at coil terminator 277. In the embodiment of FIG. 4, the LUER connector 272 is mold injected to the kink resistant tube 274. In constructing the drainage catheter of FIG. 4, an extrusion layer 279 is first used to form the substrate material. As is described below, alternatively, the substrate material could also be coated on a mandrel. This provides for a thinner substrate in applications where a thin size is required. The extruded layer 279 is then coil wrapped with the reinforcing coil 276. The LUER connector 272 is mold injected to the kink resistant tube 274.

In an alternate embodiment of the invention, the LUER connector 272 is adhesively attached or thermally bonded to the kink resistant tube. In one alternate embodiment of the invention, the LUER connector is composed of a polycarbonate. The kink resistant tube 274 is coated with a radiopaque pigmented polyurethane jacket. This polyurethane coating 278 extends from the distal end of the tapered tip 282 to the proximal end of the kink resistant tube 286.

The tapered tip 282 is provided with a number of drain holes 280. Those skilled in the art will recognize that the number of drain holes and the angular deflection and the extent of the radial deflection of the drainage end will vary based on the application of the drainage catheter. The tapered tip 282 is provided with a cannula stop 283 which prevents the cannula, which is inserted at the proximal end 285 of the LUER connector 272, from exiting the distal end of the catheter. The tapered tip 282 is heat formed by molding. The forming process also provides the cannula stop configuration.

Figure 5:
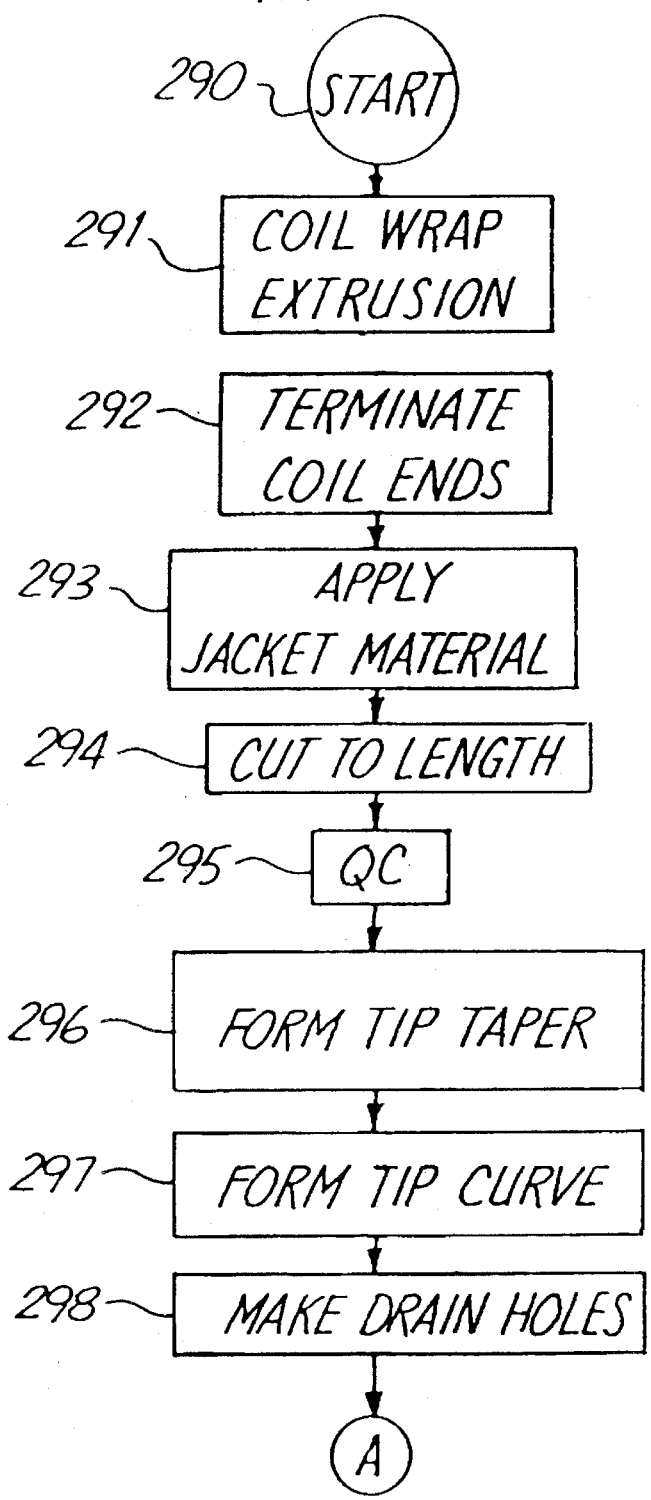
FIG. 5 shows a process flow diagram for the production and assembly of the drainage catheter of the invention.

Now referring to FIG. 5, FIG. 5 shows a process flow diagram for the production and assembly of the drainage catheter of the invention. The process starts at step 290 by coil wrapping a polyurethane extrusion. The coil wrap is then terminated at both ends in step 292. A jacket material is applied to the surface of the coil in step 293. The jacketed coil wrapped extrusion is then cut to a predetermined length in step 294. The quality of the device is then checked in step 295. The tapered tip is then heat formed in step 296 to provide a tapered tip 282 and the cannula stop 283. The process moves to step 297 to form the drainage end curve at a predetermined radius. The process then proceeds to create drain holes 280 in the tapered tip 282.

Figure 6:
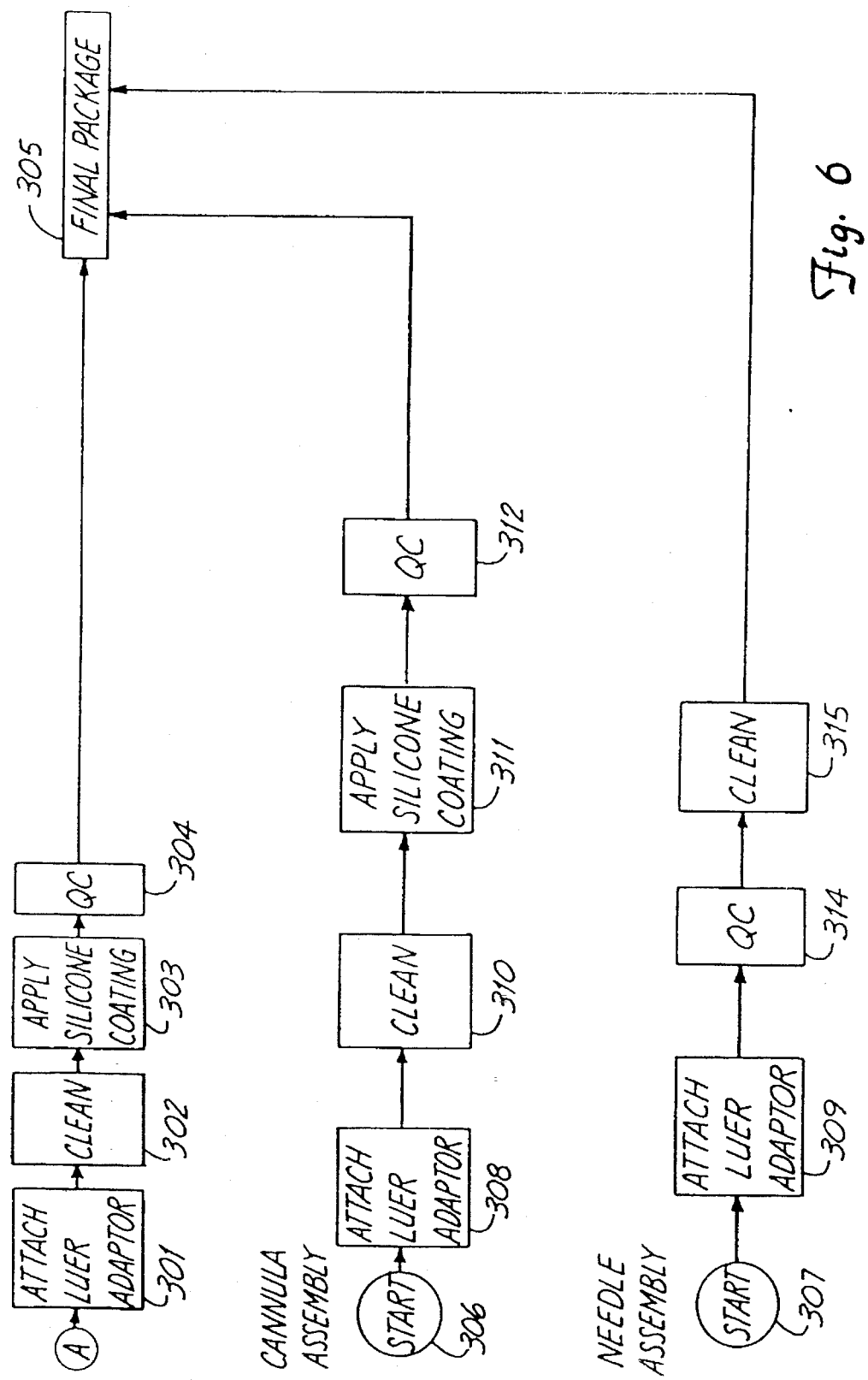
FIG. 6 shows a process flow diagram which extends the catheter assembly process of FIG. 5.

Now referring to FIG. 6, FIG. 6 extends the catheter assembly process in FIG. 5. In step 301, the LUER adaptor is attached to the kink resistant tube assembly using adhesives or heat bonding. In an alternate embodiment of the invention, the LUER adaptor is injected molded onto the kink resistant tubing section. The process continues to step 302 where the device is cleaned. In step 303, a silicon coating is applied. In step 304, the device is inspected for quality and after it passes quality inspection, and is packaged in step 305.

FIG. 6 also describes the cannula assembly process. The cannula assembly process starts in step 306 with a cannula tube. In step 308, a LUER adaptor is attached to the cannula tube. The assembly is cleaned in step 310. A silicon coating is applied to the assembly in step 311. The cannula assembly is inspected in step 312 and is packaged in step 305.

FIG. 6 also describes the needle assembly process of the invention. The needle assembly starts at step 307 with the stylet. The stylet has a LUER adapter attached to it in step 309.

Figure 7A:
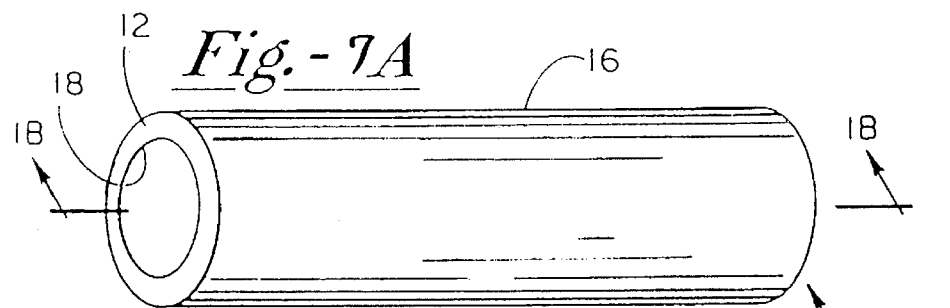
FIG. 7A shows an idealized schematic of the kink resistant tubing used in the drainage catheter apparatus of the invention.

Now referring to FIG. 7A which shows an isometric view of one embodiment of the kink resistant tube used in the drainage catheter of the invention. The kink resistant tube 10 is comprised of an ideally substantially circular inside wall 18 and an outside wall 16, which is ideally substantially perfectly smooth. The tube 10 is composed of encapsulating material 12 and an encapsulated coil 14 shown in FIG. 7B.

Figure 7B:
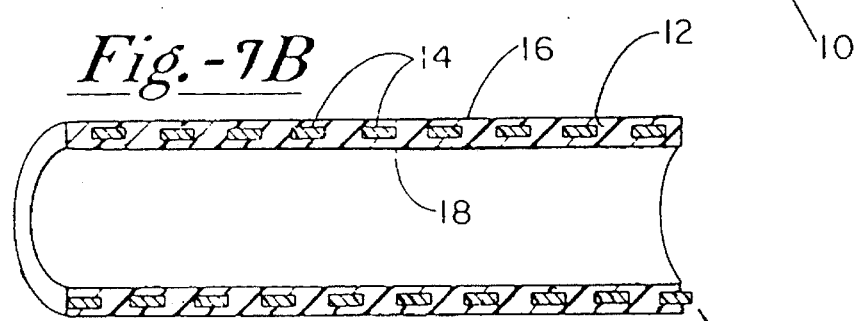
FIG. 7B shows the kink resistant tube used in the drainage catheter apparatus of the invention in an idealized cross-sectional schematic.

Now referring to FIG. 7B which shows a cross-sectional diagram of the tubing shown in FIG. 7A. FIG. 7B shows a thin walled kink resistant tube 10 constructed of an encapsulating material 12. The kink resistant tube contains a spiral wound reinforcing coil 14. FIG. 7B shows a cross-section of the tube 10 showing substantially half of the tube 10. In one embodiment of FIG. 1B the outside wall 16 is substantially smooth and parallel to the inner wall 18.

Now referring to FIG. 8A, the figure shows one embodiment of the kink resistant tube as manufactured with the kink resistant tubing construction method described below. The kink resistant tubing 20 has a ribbed surface 26 and walls comprising encapsulating material 22. The encapsulating material 22 contains a reinforcing material 24 as shown in FIG. 8B. The ribbed surface 26 comprises a plurality of ribs 25. The ribbed surface 26 closely follows the contours of the reinforcing material 24 embedded within the encapsulating material 22 of the kink resistant tubing 20. The kink resistant tubing 20 has a substantially smooth inside wall 28 through which various fluids may pass. Each of the plurality of ribs 25 is comprised of an encapsulating material around embedded reinforcing members 24.

Figure 8A:
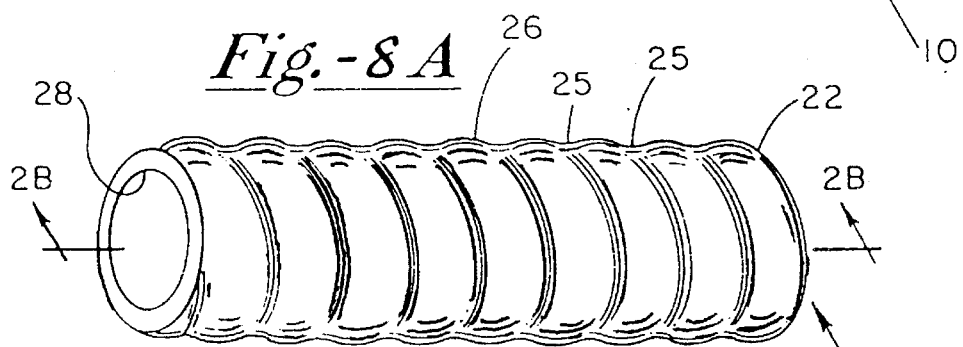
FIG. 8A shows a schematic of one example of the kink resistant tubing used in the drainage catheter apparatus of the invention
Figure 8B:
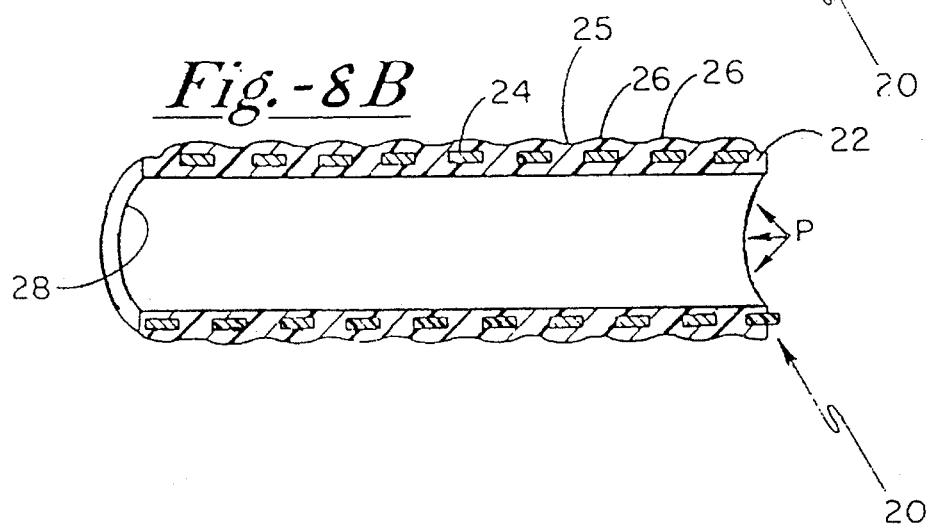
FIG. 8B shows a cross section of one example of the kink resistant tubing used in the drainage catheter apparatus of the invention.

Now referring to FIG. 8B which shows the kink resistant tubing of FIG. 8A in cross-section. The reinforcing members 24 are embedded in a thin encapsulating material 22. The reinforcing members 24 in the example embodiment of FIG. 8B are advantageously comprised of a spiral wound rectangular cross-section metallic spring which is wound around and within the encapsulating material 22. FIG. 8B also shows the plurality of ribs 25 of the outer surface 26 of the kink resistant tubing 20.

The strength and versatility of the kink resistant tube 20 is illustrated by the cross-section in FIG. 8B. The tubing is better able to withstand the hoop stresses of any internal pressure indicated by pressure arrows P on the tube wall 28. The hoop stress in the tube encapsulating material 22 is transferred to the reinforcing members 24. Those skilled in the art will recognize that the reinforcing members may either be a spiral wound spring-like structure or may be separate, individual rings independent of each other. The quality of the reinforcing material is advantageously such that the radial hoop stress is substantially and continuously absorbed radially around the tube by the reinforcing member.

Figure 9:
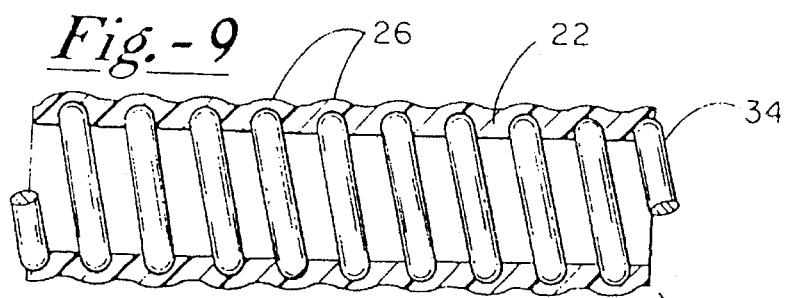
FIG. 9 shows a schematic of one example of the kink resistant tubing used in the drainage catheter as provided by the invention, further showing a plurality of reinforcing coils.

Now referring to FIG. 9 which shows the kink resistant tubing apparatus of the invention in a two-dimensional projection with the reinforcing members 34 in a top down view. FIG. 9 also shows the outside surfaces 26 of the kink resistant tubing 30. Encapsulating material 22 comprises the material between the reinforcing members 34. The reinforcing members 34 may be comprised of coiled wire made of various sizes and shapes. The encapsulating material 22 is used for the total encapsulation of the reinforcing coil 34, as the elastomeric medium, and for providing a smooth internal and external surface.

The materials of choice for the kink resistant tubing 30 are elastomers such as polyurethane or silicone rubber. Different materials may result in various levels of flexibility and kink resistance. Those skilled in the art will also recognize that when increased torque is applied to the kink resistant tubing 30, additional reinforcement in the form of multi-wire braiding, multi-filer windings and other metallic or nonmetallic reinforcement may be used.

After extensive testing in the laboratory, certain materials and material types have shown particular suitability for use in the kink resistant tubing encapsulating material. Table A lists these materials and trade names as well the manufacturers from which they are available.

TABLE A

| MATERIALS | MANUFACTURERS (TRADE NAMES) |
| --- | --- |
| (A) polyesterurethane: | B. F. Goodrich (Estane) DuPont (Hytrel) |
| (B) polyetherurethane: | Dow (Pellethane) B. F. Goodrich (Estane) |
| (C) aliphatic polyurethane: | Thermedics (Tecoflex) |

TABLE A-continued

| MATERIALS | MANUFACTURERS (TRADE NAMES) |
| --- | --- |
| (D) polyimide: | DuPont (Pyraline) |
| (E) polyetherimide: | General Electric (Ultem) |
| (F) polycarbonate: | Mobay (Apec) |
| (G) polysiloxane: | Dow Corning (Silastic) Dow Corning (MDX-4159) |
| (H) hydrophilic polyurethane: | Grace Co. (Hypol) |
| (I) polyvinyls: | commercially available |
| (J) Latex: | commercially available |
| (K) hydroxy-ethyl methacrylate: | commercially available |
| (L) blends of the above materials: | commercially available |
| (M) any other elastomer that may be carried in solvent: | commercially available |

The above-listed materials when used alone or as components to a blend of materials displayed the best performance in tubing manufactured by Navarre Laboratories Ltd. of Hamel, Minn. The subsequent products produced with these materials allow for a range of performance characteristics. Some of the blends of materials are discussed hereinbelow offered specific performance advantages.

These materials have been prepared with a solvent system material manufacturing process according to the following proportions listed in Table B. The materials listed herein are by way of illustration and not by way of limitation. Similar materials known to those skilled in the art having equivalent properties may also be used.

TABLE B

| (A) urethanes: | solids: | 64 to 14% |
| --- | --- | --- |
| | solvents: | THF/DMF 85/15 (THF - Tetrahydrofuran, DMF - Dimethylformamide) |
| | viscosity: | 10–100 centiStokes |
| (B) polyimide: | solids: | 20%–45% |
| | solvents: | N-Methylpyrrolidone |
| | viscosity: | 80–1000 centiStokes |
| (C) polyetherimide | solids: | 8% to 12% |
| | solvents: | methylene chloride |
| | viscosity: | 40–100 centiStokes |
| (D) polycarbonate: | solids: | 6% to 12% |
| | solvents: | THF/DMF 85/15 |
| | viscosity: | 10–60 centiStokes |
| (E) polysiloxane: | solids: | 30%–60% |
| | solvents: | 111-trichloroethane |
| | viscosity: | 100–450 centiStokes |
| (F) hydrophilic polyurethane: | solids: | .1%–95% |
| | solvents: | water |
| | viscosity: | not applicable |

The method by which the kink resistant tubing is fabricated will now be described in detail. The preparation of the kink resistant encapsulating materials is accomplished by following a series of steps. The preparation process is similar for all materials. The solid or liquid material is first weighed. The solvent is then prepared. The solvent is added to the solid or liquid material in the appropriate amount to make the desired percent solids. Stirring is necessary to completely solvate plastic materials. Once the plastic is completely in solution the material is ready for use in coating applications for the kink resistant tubing of the invention.

The encapsulating material 22 is configured to substantially cover the reinforcing members 34. Those skilled in the art will recognize that if a reinforcing coil having excellent bio-compatibility qualities is found, the tubing coil may not need encapsulation.

Various different types of encapsulating materials may be used to manufacture the kink resistant tubing encapsulating material. Those include, but are not limited to, polyurethane, silicone rubber, polyurethane/polycarbonate blends, polyurethane/silicone blends, polyvinylchloride, polyimide and latex.

Figure 10:
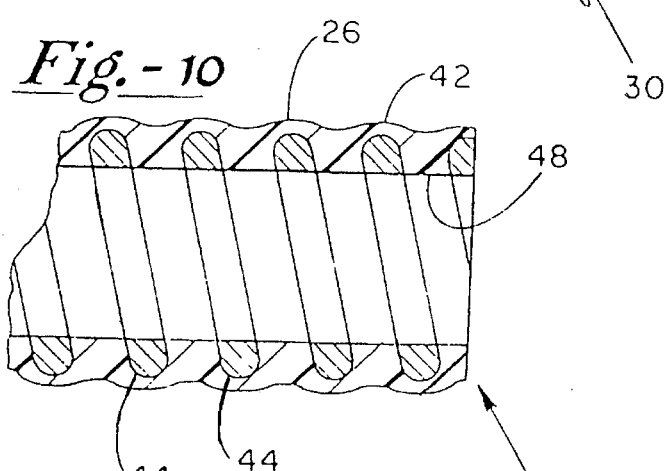
FIG. 10 shows one example of the kink resistant tubing used in the drainage catheter of the invention with a cross-sectional view of the thin wall incorporating a composite fiber reinforcement.

Now referring to FIG. 10 which shows another example of the kink resistant tubing in an enlarged cross-section diagram. The kink resistant tubing 40 has the encapsulating material 42 which in this example embodiment of the invention is advantageously substantially comprised of silicone rubber. The reinforcing members 44 comprise a composite wound fiber 44 which comprise the composite tubing's 40 coiled reinforcement member. The outer surface 26 of the composite tube 40 is formed by the encapsulating material 42.

Figure 11:
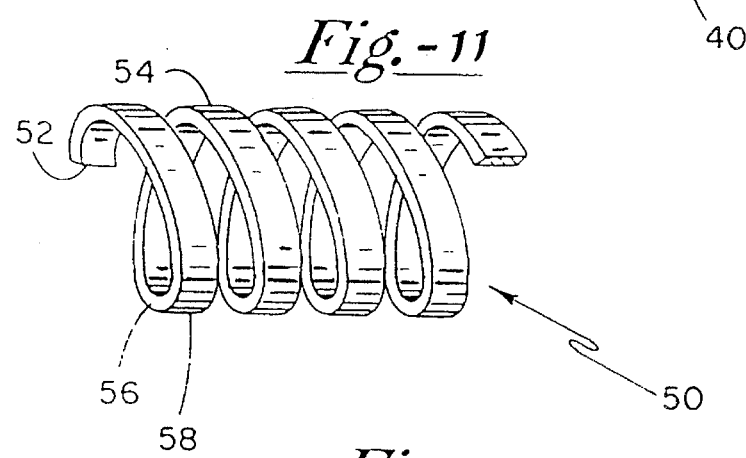
FIG. 11 shows an isometric isolation view of a supporting coil as employed in one embodiment of the invention.

Now referring to FIG. 11 which shows a schematic isometric drawing of an example of a reinforcing coil 50. The reinforcing coil 50 in the kink resistant tubing apparatus of the invention provides radial strength and hoop strength. The reinforcing coil 50 helps retain the circularity of the tubing 10 and thereby avoids buckling and kinking of the tubing 10. The reinforcing coil 50 also provides a crush-resistance to the reinforcing coil. The reinforcing coil 50 comprises a wire or fiber 54 which may have various cross-sectional shapes, such as, for example, rectangular, circular, or elliptical. Those skilled in the art will recognize that the cross-sectional shapes may affect the load bearing characteristics and strength characteristics of the reinforcing coil 50. In the example of FIG. 11 the cross-section 52 is rectangular with a flat face 56 and flat body 58 in a particularly preferred embodiment, the reenforcing coil 50 has a rectangular cross-section of from between about 0.003 inches to about 0.020 inches wide and about 0,001 inches to 0,005 inches thick, and has a pitch of about one to three times its width.

Various different reinforcing coil 50 materials may be used. Further, the reinforcing coil dimensions may be varied as may the reinforcing coil 50 pitch and diameter. Listed below in Table C are some of the alternative coil 50 design parameters that may be used.

TABLE C

| Coil Wire Size: | 0.001–0.015 |
|---|---|
| Coil Wire Material: | metals; stainless steel, MP35, NiTi, Tungsten, Platinum, kevlar, nylon, polyester, acrylic, Elgilloy (Cobalt, Chromium, Nickel, Molybdenum alloys) |
| Coil Pitch: | 1–5 times maximum coil wire dimension |
| Coil Diameter: | 0.010–0.375 inches |

Figure 12:
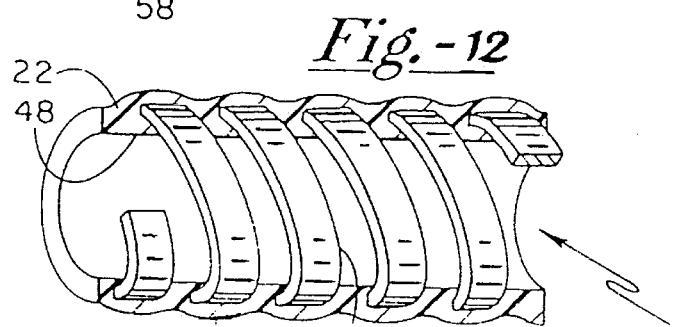
FIG. 12 shows an isometric view of the thin wall kink resistant tubing incorporating a reinforcing coil.

Referring now to FIG. 12, an isometric view of one embodiment of the kink resistant tubing 60 of the invention is shown using a wire or fiber 54. The kink resistant tube 60 construction method comprises four major steps listed in Table D. These four major process steps are described in detail below with reference to FIGS. 13–20.

TABLE D

1. Mandrel Coating
2. Coil Wrapping of Mandrel Substrate
3. Over coating the coiled assembly
4. Mandrel Extraction Now referring to FIG. 13, a mandrel 72 with a thin film encapsulating material mandrel substrate 74 is shown in a cut away view. The mandrel 72 provides the internal dimensions of the kink resistant tubing. The mandrel may be advantageously constructed from a fluoropolymer such as PTFE or FEP, polyethylene, nylon, or possibly a ductile metal such as silver. The mandrel 72 may be tubular or solid and may be advantageously diametrically reduced upon the application of sufficient stretching force. If a tubing is used for the mandrel 72, a support rod, usually metallic, may be used to provide increased straightness and stiffness.

The mandrel is coated with a thin layer or layers of the mandrel substrate 74 in solution form, using the solution draw process described below. This may require one to several coats, depending on tubing specifications and mandrel substrate 74 viscosity. Typically, inner layers are coated to thicknesses of 0.0005–0.005 inches. Solution draw rates of 6–18 inches per minute are used to apply the mandrel substrate 74.

The solution draw process is comprised of a number of steps. The first step is to prepare the encapsulating material in a solution form. The mandrel 72 is drawn through the solution of the mandrel substrate 74. The solution is held in a container and the container contains a hole slightly larger than the size of the mandrel. The mandrel is then drawn through the solution and the mandrel substrate 74 is deposited on the mandrel 72. The resulting encapsulating material thickness is highly controllable due to the propensity of the encapsulating material to adhere to the mandrel 72.

Now referring to FIG. 14 which shows a cross sectional diagram of the mandrel 72 and thin coating of mandrel substrate. 74. After the proper thickness of encapsulating material has been applied, the mandrel and encapsulating material 74 must be cured at room temperature for 6–8 hours. This allows total solvent evaporation.

The process variables for step one (mandrel coating) are summarized as follows in Table E.

TABLE E

| Environmental | |
|---|---|
| Ambient temp: | 65° F.–76° F. |
| Humidity: | 10–35% relative |
| Solution Viscosity: | 1–100 centistokes |
| Solution Draw Rate: | 6–inches per minute |
| Solvent Evaporation Rate: | 14.5 using N-Butylacetate standard |
| Solution Temp. | 65° F.–76° F. |
| Solution Chemistry | 6%–14% solids (Such as Polyurethane in solution with highly polar solvents.) |

The coil wrapping process involves wrapping the reinforcing coil wire 54 at the proper tension and pitch. The coil wire is wrapped around the coated mandrel 72 encapsulating material substrate uniformly to the desired specifications. The coil's material composition, rotational speed, tension, substrate diameter and pitch determine the size and flexibility of the coil.

Now referring to FIG. 15 which shows the method of constructing the reinforcing coil wire 54 on the mandrel substrate 74. In one embodiment of the invention, the coil wire 54 is wrapped around the mandrel 72.

Now referring to FIG. 16 which shows a cross section of the kink resistant tubing being constructed from the method of the invention. The coated mandrel substrate 74 is placed and secured in the coil wrapping apparatus 73. The coil wrapping apparatus 73 may be any suitable coil wrapping machine such as, for example, an Accuwinder (TM) machine as manufactured by the Accuwinder Company of California. The coil wire 54 must adhere to the lead end of the mandrel substrate 74 and be allowed to cure. The mandrel substrate 74 is then wrapped from end to end using the predetermined coil wrapping parameters. Once the coil wrap is complete, the coil wire 54 must be locked or secured to the coated mandrel substrate 74 using adhesives. This is done at a coil termination 77. After the adhesive has cured, the wire 54 may be cut and the coiled substrate removed from the machinery of the coil wrapping apparatus 73.

The process variables for the coiling operation include the wire wrapping speed and coil wire tension. Experimental trials have determined that the wrapping speed should be between about 500 and 4000 rpm and the coil wire tension should be between about 25 and 200 grams.

Now referring to FIG. 17 which shows the method of the invention used to apply an over coating to the coil assembly. The coil 50 is over coated to a predetermined thickness using the solution draw process described above. The process variables used in the solution draw of the encapsulating material are discussed above.

Now referring to FIG. 18 which shows the coil assembly 54 over-coated to the predetermined thickness. The solution draw process has covered the mandrel 72 forming kink resistant tubing 90 with encapsulating material. The surface 26 of the tubing 90 is formed by the outside of encapsulating material 22 solidifying around the reinforcing coil wire 54.

Now referring to FIG. 19 and FIG. 20 which show the method of the invention used to extract the mandrel 72 from the kink resistant tubing 90. Once the kink resistant tube assembly 90 has been fully cured, the final step is to extract the mandrel 72. This is done by securing each exposed termination of the mandrel 72 and applying sufficient and directionally opposite forces indicated by directional arrows 91 and 93 to plastically reduce the diameter of the mandrel 72 by 10–50%. Once this is accomplished, the mandrel 72 may simply be removed from the tubing assembly.

The invention has been described herein in considerable detail in order to comply with the Patent Statutes and to provide those skilled in the art with the information needed to apply the novel principles and to construct and use such specialized components as are required. However, it is to be understood that the invention may be carried out by specifically different equipment and devices, and that various modifications, both as to the equipment details and operating procedures, can be accomplished without departing from the scope of the invention itself.

I claim:

1. A kink resistant multi-purpose drainage catheter comprising:

(a) a thin-walled tubular substrate having a tube body having a substrate drain end and a substrate connector end, wherein the substrate drain end has a plurality of substrate drain holes;

(b) a reinforcing coil wound around a predetermined length of the tube body, the reinforcing coil having a rectangular cross section of from between about 0.003 inches to about 0.020 inches wide and about 0.001 inches to about 0.005 inches thick and the coil having a pitch of 1 to 3 times its width; and (c) a thin-walled tubular jacket covering the reinforcing coil having a jacket drain end covering the substrate drain end and a jacket connector end covering the substrate connector end such that the jacket drain end forms a predetermined drainage shape, and wherein the tubular jacket has a plurality of jacket drain holes disposed to allow fluid to drain through the substrate drain holes into the kink resistant multi-purpose drainage catheter; and (d) a connector attached to the jacket connector end.

2. The kink resistant multi-purpose drainage catheter of claim 1 wherein the connector further comprises a LUER connector.

3. The kink resistant multi-purpose drainage catheter apparatus of claim 1 wherein the plurality of jacket drain holes are located on a same side of the tubular jacket.

4. The kink resistant multi-purpose drainage catheter of claim 1 wherein the plurality of jacket drain holes are evenly spaced over the length of the jacket drain end.

5. The kink resistant multi-purpose drainage catheter of claim 1 wherein the jacket drain end is curved at a predetermined radius to form substantially a "J" shape.

6. The kink resistant multi-purpose drainage catheter of claim 1 wherein the jacket drain end is curved in a "pigtail" shape.

7. The kink resistant multi-purpose drainage catheter of claim 1 wherein the connector is attached to the jacket connector end by an adhesive.

8. The kink resistant multi-purpose drainage catheter of claim 1 wherein the connector is attached to attached to the jacket connector end by thermal bonding.

9. The kink resistant multi-purpose drainage catheter of claim 1 wherein the tubular substrate comprises a soft plastic elastomer.

10. The kink resistant multi-purpose drainage catheter of claim 1 wherein the tubular jacket comprises a soft plastic elastomer.

11. The kink resistant multi-purpose drainage catheter of claim 1 wherein the reinforcing coil is selected from the group consisting of stainless steel, kevlar, Cobalt-Chromium-Nickel-Molybdenum alloy, NiTi, Tungsten, Platinum, nylon, polyester, acrylic.

* * * * *